United States Patent [19]

Secrist, III et al.

[11] 3,960,840

[45] June 1, 1976

[54] FLUORESCENT DERIVATIVES OF ADENINE-CONTAINING COMPOUNDS

[75] Inventors: John A. Secrist, III, Cambridge, Mass.; Jorge R. Barrio; Nelson J. Leonard, both of Urbana; Gregorio Weber, Urbana, all of Ill.

[73] Assignee: University of Illinois Foundaton, Urbana, Ill.

[22] Filed: Dec. 29, 1972

[21] Appl. No.: 319,744

[52] U.S. Cl. .................... 260/211.5 R; 204/158 R; 424/7
[51] Int. Cl.² ................. C07H 19/16; C07H 19/20
[58] Field of Search ............................ 260/211.5 R

[56] References Cited
UNITED STATES PATENTS

| | | | |
|---|---|---|---|
| 3,462,416 | 8/1969 | Hanze et al. ................. | 260/211.5 R |
| 3,701,772 | 10/1972 | Tamura et al. ................ | 260/211.5 R |
| 3,712,885 | 1/1973 | Weimann et al. ............. | 260/211.5 R |
| 3,872,098 | 3/1975 | Jones et al. .................. | 260/211.5 R |

OTHER PUBLICATIONS

Kochetkov et al., "Chem. Abst.," vol. 75, 1971, p. 64,183t.
Barrio; Jorge R., Biochemical and Biophysical Research Communications, vol. 46, No. 2, 1972.

*Primary Examiner*—Johnnie R. Brown
*Attorney, Agent, or Firm*—Merriam, Marshall, Shapiro & Klose

[57] ABSTRACT

Fluorescent analogs of biologically active coenzymes are made by reaction of certain adenine-containing coenzymes with acetaldehyde. The reaction products retain a substantial portion of their biologic activity and are fluorescent in the visible range under ultraviolet illumination.

6 Claims, No Drawings

FLUORESCENT DERIVATIVES OF ADENINE-CONTAINING COMPOUNDS

The invention described herein was made in the course of, or under, a grant from the National Institutes of Health, Department of Health, Education, and Welfare.

BRIEF DESCRIPTION OF THE INVENTION

This invention relates to certain novel biologically active coenzymes which are fluorescent within the visible range, to a method for making these compounds, and to a method for rapid detection of adenine-containing biologic residues in admixture with other compounds.

Certain adenosine-containing coenzymes, such as the mono-, di-, and triphosphate derivatives of adenosine and the anhydrides of such compounds with nicotinamide mononucleotide and flavin mononucleotide, play indispensable roles in living organisms. Such compounds act as universal stoichiometric coupling agents between metabolic sequences, as regulatory modifiers of these sequences, and as the means for energy utilization and storage in metabolic sequences. The fluorescent compounds of the invention are analogs of these coenzymes and exhibit enzymatic activity similar to that of each parent compound, thus permitting the fluorescent analogs to be substituted for the parent compounds in investigating the interaction of these coenzymes with macromolecules in biological systems. The fluorescent properties of the compounds permit ready detection of the coenzymes in such systems.

In general, the fluorescent coenzymes of the invention are prepared from the analogous non-fluorescent parent compounds by introducing an etheno bridge (—CH=CH—) between the 1- and the $N^6$-positions of the adenine ring present in the compounds. This result is achieved by reacting the parent compound with a solution of chloroacetaldehyde. The compounds produced by this process have fluorescence which occurs within the visible spectrum and which has a relatively long lifetime. Most importantly, the modified compounds continue to exhibit substantial enzymatic activity, thus permitting the fluorescent analogs to be used as probes in systems in which the parent non-fluorescent compounds are involved. The fluorescent properties of these compounds also permit the ready detection of adenine-containing compounds in a mixture of coenzymes.

DETAILED DESCRIPTION OF THE INVENTION

The fluorescent coenzymes of the invention consist of the general formula

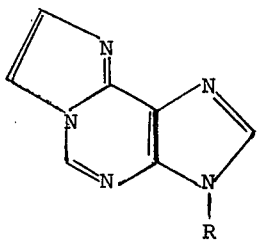

wherein R has any of the following formulas:
A. those having (1)

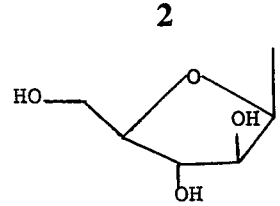

(2)

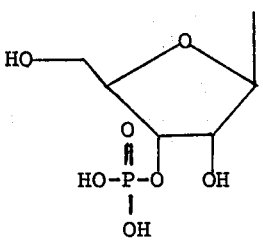

(3)

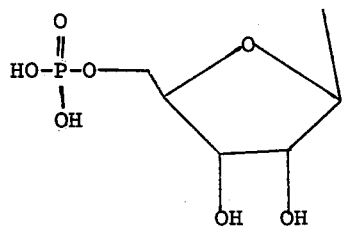

(4)

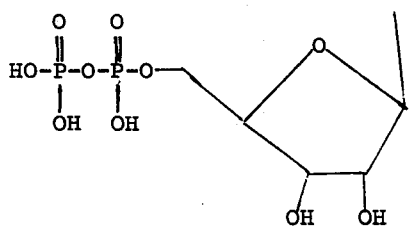

(5)

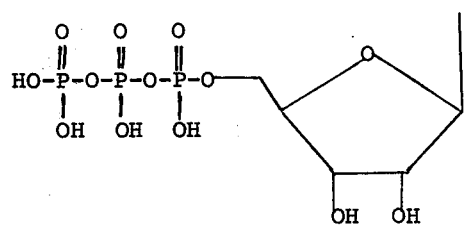

(6)

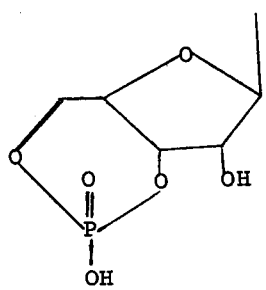

B. anhydrides of A(3) above, with nicotinamide mono-nucleotide or flavin mononucleotide, and dinucleoside phosphates derived therefrom, and C. salts of any of the compounds of Groups A and B above.

It will be seen that the compounds of the invention are derivatives of adenine or adenosine, in which an etheno (—CH=CH—) bridge is present between the 1- and $N^6$-positions of the adenine ring. The abbreviation "$\epsilon$", representing "etheno", will be used herein to refer to this etheno bridge, and using this nomenclature, the novel compounds of Group A above can be designated as 1. 1,$N^6$-ethenoarabinosyladenine (ara-$\epsilon$A)
2. 1,$N^6$-ethenoadenosine-3'-monophosphate (3'-$\epsilon$AMP)
3. 1,$N^6$-ethenoadenosine-5'-monophosphate (5'-$\epsilon$AMP)
4. 1,$N^6$-ethenoadenosine-5'-diphosphate (5'-$\epsilon$ADP)
5. 1,$N^6$-ethenoadenosine-5'-triphosphate (5'-$\epsilon$ATP)
6. 1,$N^6$-ethenoadenosine-3',5'-cyclic monophosphate (3',5'-cyclic-$\epsilon$AMP).

The members of Group (B) above are 1,$N^6$-ethenonicotinamide adenine dinucleotide ($\epsilon$NAD$^+$) and flavin-1,$N^6$-ethenoadenine dinucleotide ($\epsilon$FAD). These compounds are anhydrides of 5'-$\epsilon$AMP with nicotinamide mononucleotide or flavin mononucleotide, both of which are known materials. The members of Group C are salts, which can be made from the novel compounds of the invention in conventional fashion, by neutralizing one or more acid groups which may be present in the compound with an inorganic base, such as NaOH. In addition, acid addition salts can be made by reacting the compound with an inorganic acid, such as HCl.

The novel fluorescent coenzymes of the invention are prepared by reacting the parent coenzyme (e.g., ATP) with chloroacetaldehyde to introduce the 1,$N^6$-etheno bridge into the adenine ring. The reaction takes place readily in solution at a pH within the range of about 1–8, and preferably about 3.5–5.5, and proceeds quantitively to completion over a period of about 24–72 hours. The temperature of reaction is not critical; any temperature above the freezing point of the solution to the boiling point of chloroacetaldehyde (85°C.) can be used, although a preferred temperature range is about 20°–50°C. and room temperature is usually suitable.

For forming the solution of the coenzyme and chloroacetaldehyde, any solvent which is compatible with the reactants can be used. Water is preferred, although organic solvents, such as ethanol, isopropyl alcohol, dimethyl formamide, and acetonitrile, can also be used. The concentration of the solution is similarly not critical and is limited only by the solubility of the reactants in the selected solvent. Concentrations on the order of 1.0–2.0 molar are typical and can be used effectively.

EXAMPLES

Illustrative of the compounds of the invention are those whose properties are given below in Table I. These compounds were prepared by stirring a solution of 2 millimoles of the adenosine derivative in 20 ml. of 2M aqueous chloroacetaldehyde at pH 4.0–4.5, for 24–72 hours at a temperature of 20°–72°C. The resulting reaction product was decolorized with charcoal and evaporated to dryness under vacuum. Reprecipitation of the residue from aqueous ethanol was followed by an ethanol wash to yield pure product. The compounds listed in Table I were made following this method. Each pure product was characterized by analysis, chromatography, and spectroscopic methods.

TABLE I

| Compound | Formula and Molecular Wt. | Analysis | | Fluorescence Data, nm (Neutral) |
|---|---|---|---|---|
| | | Calcd. | Found | |
| 5'-$\epsilon$AMP | $C_{12}H_{14}N_5O_7P \cdot H_2O$ | %C: 37.02 | 36.90 | 410 |
| | | %H: 4.14 | 4.08 | |
| | 389.27 | | | |
| 3'-$\epsilon$AMP | $C_{12}H_{14}N_5O_7P \cdot H_2O$ | %C: 37.02 | 37.11 | 410 |
| | | %H: 4.14 | 4.39 | |
| | 389.27 | | | |
| 3'5'-cyclic-$\epsilon$AMP | $C_{12}H_{12}N_5O_6P \cdot H_2O$ | %C: 38.82 | 38.90 | 410 |
| | | %H: 3.80 | 3.62 | |
| | 371.25 | | | |
| $\epsilon$ADP (Na Salt) | $C_{12}H_{14}N_5O_{10}P_2Na \cdot H_2O$ | %C: 29.34 | 29.54 | 410 |
| | | %H: 3.28 | 3.40 | |
| | 491.24 | | | |
| $\epsilon$ATP (di-Na Salt) | $C_{12}H_{14}N_5O_{13}P_3Na_2 \cdot 2H_2O$ | %C: 23.58 | 24.03 | 410 |
| | | %H: 2.97 | 3.17 | |
| | 611.22 | | | |
| $\epsilon$NAD$^+$ | $C_{23}H_{27}N_7O_{14}P_2 \cdot 3H_2O$ | %C: 37.26 | 37.16 | 410 |
| | | %H: 4.49 | 4.48 | |
| | 741.51 | | | |

As indicated in Table I, the compounds of the invention are strongly fluorescent, having a maximum emission in the visible spectrum, at about 410 nm. in buffered aqueous solution at pH 7.0, and a fluorescence lifetime of about 20 nsec. All of the compounds of the invention with the exceptions of $\epsilon$NAD$^+$ and $\epsilon$FAD have similar fluorescence properties.

The ethenoadenosine derivatives of the invention have been found to possess a substantial portion of the enzymatic activity of the normal substrates. The enzymatic activity of these compounds is exemplified by the data contained in Table II for $\epsilon$ATP and $\epsilon$ADP. In this work the enzyme assays were performed with a spectrophotometer at 26°C. Values of $V_{max}$ and $K_m$ were calculated from the experimental data using a computer employing a least-squares program.

Pyruvate Kinase (Spectrophotometric Determination of ADP or $\epsilon$ADP). These assays were performed in a medium containing 100 mM Tmates [tetramethylammonium-N-tris-(hydroxymethyl)methyl-2-aminoethanesulfonic acid buffer, pH 7.5], 100 mM KCl 5mM MgCl$_2$, 2 mM phosphoenolpyruvate, 0.2 mM NADH, lactate dehydrogenase, pyruvate kinase, following the decrease in absorbance at 340 nm. ADP or εADP was used at concentrations varying from 0.1 to 2.0 mM.

Andenylate Kinase (Myokinase). The reaction was assayed by coupling the production of ADP (or εADP) to pyruvate kinase and lactate dehydrogenase and following the oxidation of NADH at 340 nm. The assay mixture (1 ml) contained 50 mM Tris-HCl buffer (pH 8.0), 5 mM $MgCl_2$, 25 mM KCl, 1 mM phosphoenolpyruvate, 0.2 mM NADH, pyruvate kinase, lactate dehydrogenase, AMP (1.0 mM) or εAMP-ATP (0.01–0.1 mM) or εATP (0.1–2.0 mM). The reaction was started by the addition of 0.05 μg of myokinase/ml.

Hexokinase. The experiments were done by coupling the production of glucose 6-phosphate with glucose-6-phosphate dehydrogenase. The reaction rate was determined by measuring the reduction of $NADP^+$ at 340 nm. The experiments were carried out with 1 ml of reaction mixtures containing 100 mM Tris-HCl buffer (pH 8.0), 6 mM $MgCl_2$, 1 mM glucose, 1 unit of glucose-6-phosphate dehydrogenase, 0.2 mM $NADP^+$-ATP (0.005–0.5 mM) or εATP (0.4–3 mM). The reactions were initiated by addition of 0.04 unit of hexokinase for ATP and 0.2 unit for εATP.

Phosphofructokinase. The assay mixture contained in a final volume of 1 ml: 100 mM Pipes buffer [piperazine-N,N-bis(2-ethanesulfonic acid) monosodium salt, pH 6.9], 6 mM $MgCl_2$, 50 mM KCl, 0.3 mM fructose 6-phosphate, 2 mM phosphoenolpyruvate, 0.2 mM NADH, 1 unit of pyruvate kinase, 2 units of lactate dehydrogenase, ATP or εATP (0.01–0.1 mM for either). The reaction was initiated by the addition of 0.06 unit of phosphofructokinase. For the phosphofructokinase inhibition studies, 12 mM $MgCl_2$ was used, with all the other ingredients the same as the above and the appropriate dilutions of ATP or εATP.

Table II

Kinetic Data for ε Coenzymes

| Enzyme | Substrate | Binding Constant, $K_m$ (mM)* | Activity, $V_{max}$** |
|---|---|---|---|
| Hexokinase (yeast) | εATP | 2.0 (0.12) | 0.38 |
| Phosphofructokinase (rabbit muscle) | εATP | 0.030 (0.013) | 0.95 |
| Pyruvate kinase (rabbit muscle) | εADP | 0.30 (0.30) | 0.80 |
| Adenylate kinase (rabbit muscle) | εATP | 1.85 (0.07) | 0.83 |

*$K_m$ for normal substrate in parentheses.
**Relative to normal substrate.

As shown in Table II, the representative fluorescent analogs of the invention (εADP and εATP) had activities equal to 38–95% of those of the non-fluorescent parent compounds (i.e., ADP and ATP). Other fluorescent compounds of the invention show the same range of activities.

The visible fluorescence properties of the compounds of the invention form the basis for a method for rapid detection of adenine-containing residues. In accordance with this aspect of the present invention, etheno derivatives of adenine-containing compounds are prepared in situ from the parent compounds by reaction with a solution of chloroacetaldehyde. The appearance of fluorescence when the treated material is illuminated by an ultraviolet lamp established the presence of adenine-containing residues. The degree of fluorescent can also be used as an approximation of the amount of adenine-containing residues in the treated material.

This method of the invention is applicable to the detection of certain adenine-containing naturally occuring coenzymes, either in solution or chromatograms prepared by paper chromatography, thin-layer chromatography, or paper electrophoresis. Since the fluorescent derivatives of the adenine-containing residues can be made easily at mild ambient conditions, the method as applied to a solution containing coenzymes involves adding to the solution a sufficient quantity of a solution of chloroacetaldehyde at a pH within the range of 1 to 8. In the case of chromatograms, the solution of chloroacetaldehyde is sprayed onto the chromatogram. In both cases the treated material is subjected to illumination by an ultraviolet lamp, and the existence of visible fluorescence confirms the presence of an adenine-containing moiety in the original mixture.

The method of the invention is illustrated by the following examples. The major nucleosides, cytidine, uridine, adenosine and guanosine, were spotted both separately and as a mixture on cellulose thin-layer plates and developed with isopropanol-water (7:3, v/v). The chromatograms were dried, sprayed with a 1.5 M solution of chloroacetaldehyde in water at pH 2.0, and placed in suitable loosely-covered jars containing a small amount of chloroacetaldehyde solution in the bottom. The jars were warmed in an oven at 70°C. for 15 minutes. The chromatograms were illuminated from above with an ultraviolet lamp for detection. Only the adenine-containing compounds exhibited fluorescene in the visible range, thus permitting the detection of these compounds. By a similar procedure using isobutyric acid-$NH_4OH$-water (75:1:24, v/v/v) as solvent, ATP, ADP, 5'-AMP, 3'-AMP and cyclic AMP are readily distinguished in mixtures with other non-adenine-containing moieties.

A bidimensional thin-layer chromatography system (Eastman Chromagram cellulose sheets without fluorescent indicator) was used for a dinucleotide mixture containing ApU, UpC, CpA, ApP, GpC, ApA, and CpC. Development was carried out first with isobutyric acid-$NH_4OH$-water (75:1:24, v/v/v) followed by isopropanol-$NH_4OH$-water (7:1:2, v/v/v) for the second dimension. Treatment of the developed plate allowed fluorescent detection of only the adenine-containing dinucleotides, determined by following the procedure given above. This procedure was found to work equally well with paper chromatograms. The visual detection limit obtained for the assayed compounds with this fluorigenic method is about 0.5 microgram. Additionally, such a procedure serves to detect adenine-containing residues in solution at concentrations in the range of about $10^{-8}$ molar.

The foregoing detailed description has been given for clearness of understanding only, and no unnessary limitations should be understood therefrom, as modifications will be obvious to those skilled in the art.

We claim:

1. A biologically active coenzyme which is fluorescent within the visible spectrum, said coenzyme being selected from the group consisting of:

A. compounds having the formula

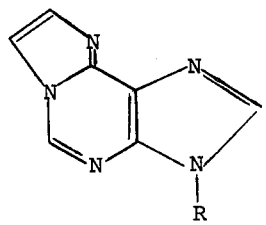

wherein R has any of the following formulas:

(1) 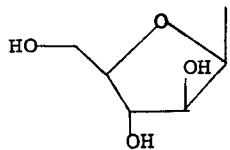

(2) 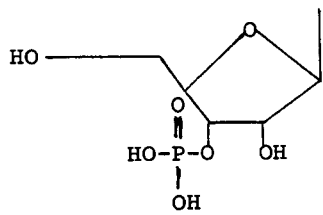

(3) 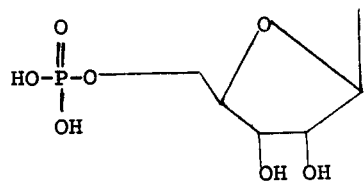

(4) 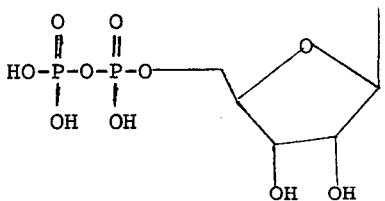

(5) 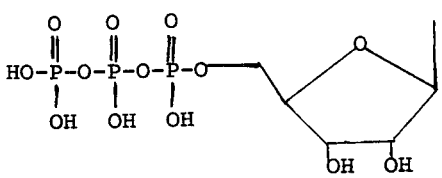

B. anhydrides of A(3) above with nicotinamide mononucleotide or flavin mononucleotide, and
C. salts of any of the compounds of Groups A(2-)–A(5) or (B) above with inorganic bases.
2. 1,$N^6$-ethenoadenosine 5'-monophosphate.
3. 1,$N^6$-ethenoadenosine 3'-monophosphate.
4. 1,$N^6$-ethenoadenosine 5'-diphosphate.
5. 1,$N^6$-ethenoadenosine 5'-triphosphate.
6. 1,$N^6$-ethenoarabinosyladenine.

* * * * *

UNITED STATES PATENT AND TRADEMARK OFFICE
CERTIFICATE OF CORRECTION

PATENT NO. : 3,960,840
DATED : June 1, 1976
INVENTOR(S) : John A. Secrist et al.

It is certified that error appears in the above-identified patent and that said Letters Patent are hereby corrected as shown below:

Col. 1, line 54, after "consist of" and before "the general formula" insert
        --(A) those having--

Col. 1, line 67, cancel "A. those having"

Col. 5, line 66, " established " should be
        -- establishes --

Col. 5, line 68, "fluorescent" should be
        --fluorescence--

Col. 6, line 29, "fluorescene" should be
        --fluorescence--

Signed and Sealed this

Tenth Day of August 1976

[SEAL]

*Attest:*

RUTH C. MASON
*Attesting Officer*

C. MARSHALL DANN
*Commissioner of Patents and Trademarks*